United States Patent
Guo et al.

(10) Patent No.: US 11,714,042 B1
(45) Date of Patent: Aug. 1, 2023

(54) REVERSIBLE PLUGGING-TYPE DEVICE FOR PREVENTING SEEPAGE FROM SIDE WALL OF IRREGULAR SAMPLE

(71) Applicant: Southwest Petroleum University, Chengdu (CN)

(72) Inventors: Liang Guo, Chengdu (CN); Baoquan Wang, Chengdu (CN); Jinfeng Wu, Chengdu (CN); Haixu Wen, Chengdu (CN); Jiaheng Xie, Chengdu (CN); Min Zhang, Chengdu (CN); Yiqi Peng, Chengdu (CN); Jinlong Zhao, Chengdu (CN); Xingzhu Lin, Chengdu (CN); Ang Li, Chengdu (CN)

(73) Assignee: Southwest Petroleum University, Sichuan (CN)

( * ) Notice: Subject to any disclaimer, the term of this patent is extended or adjusted under 35 U.S.C. 154(b) by 0 days.

(21) Appl. No.: 18/099,944

(22) Filed: Jan. 22, 2023

(30) Foreign Application Priority Data

Apr. 1, 2022 (CN) .......................... 202210348834.6

(51) Int. Cl.
*G01N 15/08* (2006.01)
(52) U.S. Cl.
CPC .................. *G01N 15/0806* (2013.01)
(58) Field of Classification Search
CPC ..... G01N 15/00; G01N 15/08; G01N 15/0806
See application file for complete search history.

(56) References Cited

FOREIGN PATENT DOCUMENTS

| CN | 106680022 A | * | 5/2017 | ............... G01N 1/08 |
| CN | 112595648 A | * | 4/2021 | ............. G01N 15/08 |
| CN | 113155702 A | * | 7/2021 | ............. G01N 15/08 |
| CN | 114544458 A | * | 5/2022 | ............. G01N 15/08 |

* cited by examiner

*Primary Examiner* — Nguyen Q. Ha
(74) *Attorney, Agent, or Firm* — Swope & Yuy Ang IP Law Group (57) ABSTRACT

The application discloses a reversible plugging-type device for preventing seepage from a side wall of an irregular sample (14), comprising a sleeve (15) with both ends open, a primary lantern ring (4), a secondary lantern ring (5), a tertiary lantern ring (26) and a rotation shaft (1) arranged in a barrel (2), a lower end surface of the barrel (2) is provided with an annular floating plate (17), the primary lantern ring (4), the secondary lantern ring (5), and the tertiary lantern ring (26) are hollow, first phase liquid pipe (7) is arranged on a lower end surface of the primary lantern ring (4), second phase liquid pipe (8) is arranged on a lower end surface of the secondary lantern ring (5), the first phase liquid pipe (7) and the second phase liquid pipe (8) extend downward toward a mixing pipe (10). The floating plate (17) has the mixing pipe (10), which runs through the floating plate (17) and has a discharging pipe (22) provided with a discharge port (23).

9 Claims, 3 Drawing Sheets

FIG. 5

REVERSIBLE PLUGGING-TYPE DEVICE FOR PREVENTING SEEPAGE FROM SIDE WALL OF IRREGULAR SAMPLE

TECHNICAL FIELD

The application relates to the technical field of seepage testing, in particular to a reversible plugging-type device for preventing seepage from a side wall of an irregular sample.

BACKGROUND

The flow of fluid (such as water, oil, etc.) through porous media is called seepage. The porous medium refers to the material composed of solid skeleton and interconnected pores and cracks, such as rock mass and soil mass. Seepage will affect the physical and mechanical properties of rock mass and soil mass. Groundwater is an important geological agent, its interaction with rock mass and soil mass, on the one hand, changes the physical, chemical and mechanical properties of rock mass and soil mass, while on the other hand, changes the physical, mechanical properties and chemical components of groundwater itself. Therefore, the study of rock or soil seepage plays a vital role in controlling the quality of geotechnical engineering construction and understanding the effect of geotechnical construction, and can provide data support for further geotechnical utilization.

When performing seepage tests on rock or soil, using a cylindrical sampler (test device) to obtain indoor seepage is the most common test method for studying the hydraulic properties of rock and soil. However, for coarse-grained soil and irregular rock samples with low adhesion, due to the different particle sizes, they cannot fully fit when in contact with the inner wall of the cylindrical sampler (test device), creating dominant seepage channels of large pores; because the fluid passes through the dominant channels on the side wall of the sample rather than completely through the rock and soil sample, it is difficult to objectively reflect the actual seepage characteristics of the research object. Some testers usually apply latex or oil pressure on the inner wall of the test device before sampling to seal and block water, but even so, the experimental data still have large deviations.

SUMMARY

The object of the present application is to provide a reversible plugging-type device for preventing seepage from a side wall of an irregular sample to solve the above problems.

The present application is realized through the following technical solutions:

a reversible plugging-type device for preventing seepage from a side wall of an irregular sample, comprises a sleeve with both ends open, a barrel arranged on an upper end of the sleeve, a base arranged below the sleeve, a primary lantern ring, a secondary lantern ring, a tertiary lantern ring and a rotation shaft are fixedly arranged in the barrel along the radial direction of the barrel in sequence from the outside inward, a lower end surface of the barrel is provided with an annular floating plate, each of the primary lantern ring, the secondary lantern ring, and the tertiary lantern ring is internally hollow, at least one first phase liquid pipe is arranged on a lower end surface of the primary lantern ring, and at least one second phase liquid pipe is arranged on a lower end surface of the secondary lantern ring, lower ends of the first phase liquid pipe and the second phase liquid pipe extend vertically downward;

a winding ring is arranged circumferentially in the tertiary lantern ring, a heat-shrinkable film has one end circumferentially wound on an outer circumferential wall of the winding ring, and the other end extending downward after running through a lower end surface of the tertiary lantern ring and a middle part of the floating plate, the floating plate is provided with a mixing pipe which is communicated with the first phase liquid pipe and the second phase liquid pipe respectively, a lower end of the mixing pipe runs through the floating plate and is provided with a discharging pipe, the discharging pipe has a closed lower end and is provided with a discharge port facing a center line of the barrel on a side wall. In the prior art, when studying the hydraulic properties of rock and soil, it is necessary to clamp and place a columnar sample on the seepage tester, and then obtain relevant seepage data through pressurized water injection, so as to realize the quality control of geotechnical engineering construction, avoid disasters such as landslides or mudslides, and at the same time to understand the effect of geotechnical construction in time, and provide data support for further rock and soil utilization; however, at present, the seepage pressure chamber of rock and soil mass is only capable of testing cylindrical standard specimens, and has not yet broken through the technical difficulties of preventing seepage from a side wall of an irregular sample. Due to the data deviation caused by the leakage between the sample and the side wall of a sleeve in the indoor seepage test, the obtained results are difficult to reflect the objective seepage characteristics of the soil sample, and it is impossible to meet the requirements for indoor test of irregular and nonstandard fractured rock. Therefore, to provide an efficient solution for this, the applicant designed a side wall anti-seepage device, which is specially used for the anti-seepage treatment of the sample side wall before seepage test of the irregular sample, so as to avoid the seepage from the side wall of a sample during the test by a seepage detector, which improves the accuracy of the test data.

During the specific operation, the base completely seals the lower end of the sleeve, the irregular sample is placed on the upper surface of the base, the barrel is vertically inserted into the sleeve, and an external motor drives a rotation shaft and the barrel to move in a circumferential direction. An external cylinder drives the barrel to move up and down in the sleeve, and a floating plate is provided below the barrel through a connecting rod, and the distance between the lower end surface of the barrel and the upper surface of the floating plate can be changed by changing the length of the connecting rod. When performing anti-seepage treatment, the heat-shrinkable film is first removed from the tertiary lantern ring and moves vertically downward along the axis of the barrel, and the columnar heat-shrinkable film is directly sleeved on the periphery of a sample after passing through the middle of the floating plate, until the lower end of the heat-shrinkable film wraps the irregular sample completely, the heat-shrinkable film stops moving, and at the same time the barrel and the floating plate move down to near the upper surface of the base, at this time, the interior of the primary lantern ring is filled with a component liquid A, the secondary lantern ring is filled with a component liquid B, and the two component liquid enter the sleeve through the first phase liquid pipe and the second phase liquid pipe respectively. The floating plate is also provided with a mixing pipe which is communicated with the first phase liquid pipe and the second phase liquid pipe respectively. A discharge pipe is located below the floating plate, and a discharge port of the discharge pipe is facing the axis of the floating plate. The external motor drives the barrel to rotate slowly while the external cylinder drives the barrel to move upward, and a pressurized pipe is connected to the mixing pipe to ensure that the flow rate and flow velocity of the two component liquid flowing from the mixing pipe into the discharge pipe are greater than the liquid flow rate in the first phase liquid pipe and the second phase liquid pipe, that is, the foam material ejected from the discharge port is formed in a short time, and the liquids in the first phase liquid pipe and the second phase liquid pipe start to produce a chemical reaction at the bottom of the barrel, and the heat released therefrom can heat the heat-shrinkable film covering the sample step by step from top to bottom along the axis of the barrel, so that the columnar heat-shrinkable film is tightly attached to the outer wall of the sample, and at the same time, the liquid in the discharge pipe is foamed before the mixed liquid at the bottom of the sleeve, and the formed foaming colloid is wound on the outer wall of the heat-shrinkable film in a spiral state, and the foaming colloid formed by the liquid between the sample and the inner wall of the sleeve will completely fill the annular space, so as to ensure that the outer wall of the sample is covered by the heat-shrinkable film, while the foaming colloid keeps squeezing the sample and the heat-shrinkable film, and the floating plate is kept above the annular part between the sample and the inner wall of the sleeve, to prevent the foaming colloid from changing irregularly in the vertical upward direction, ensure that the two ends of the sample after the anti-seepage treatment are flush, and facilitate the perfect docking with the detection part of the seepage tester.

In this technical solution, a two-component polyurethane foam material is used, wherein the component liquid A is a mixed liquid of a foaming agent, a foam stabilizer, a catalyst and polyether polyol, and the component liquid B is isocyanate, the two component liquids are mixed at a fixed ratio, and can react to form polyurethane foam colloid in normal temperature environment, while releasing heat to make the heat-shrinkable film shrink. The polyurethane foam colloid has good filling effect, uniform texture, and a foaming ratio of 3-5 times, which is completely applicable for anti-seepage treatment on the side wall of the sample. The heat-shrinkable film is arranged in the same way as a roll of fresh-keeping bag, that is, discontinuous incisions are set at a fixed distance to facilitate the cutting of the heat-shrinkable film.

An electromagnetic valve is arranged in the first phase liquid pipe and the second phase liquid pipe respectively, and the electromagnetic valve is located below a portion where the mixing pipe is respectively connected with the first phase liquid pipe and the second phase liquid pipe. The electromagnetic valves are arranged in the first phase liquid pipe and the second phase liquid pipe respectively, and the liquid in the annular space and the mixed liquid in the discharge pipe are kept at different release speed, so as to intuitively and effectively control the forming speed of the foaming colloid in the discharge pipe and the foaming colloid in the annular space, thereby fulfilling the purpose of anti-seepage treatment on the side wall of the sample.

The horizontal heights of the lower end of the first phase liquid pipe and the lower end of the second phase liquid pipe are higher than the horizontal height of the discharge port. Optionally, the liquid discharge speed of the liquid in the first phase liquid pipe and the second phase liquid pipe is controlled, while the liquid discharge height of the liquid in the first phase liquid pipe and the second phase liquid pipe is also set to be different from the discharge height of the mixed liquid in the discharge pipe, so as to ensure that there is a minor difference between the forming speed of the foaming colloid in the annular space and that of the foaming colloid overflowing from the discharge port, so as to realize the goal of preliminary bondage of the heat-shrinkable film and the sample, and then the overall wrapping.

A magnetic ring is provided on an extension end of the heat-shrinkable film, an annular groove matching the magnetic ring is provided on an upper surface of the base. The magnetic ring arranged at the lower end of the heat-shrinkable film can not only increase the weight at the lower end of the heat-shrinkable film, but also attract the metal annual groove arranged on the upper surface of the base to prevent the foaming colloid in the annular space from passing through the bottom of the sample, while ensuring that the heat-shrinkable film in the tertiary lantern ring protrudes freely during the upward movement of the barrel, and the lower end of the heat-shrinkable film attached to the upper surface of the base will not be displaced with the upward movement of the barrel.

A rubber ring is circumferentially provided on the inner circumferential wall of the floating plate and has an inner diameter greater than the outer diameter of the magnetic ring. Because the sample has an irregular shape, the irregular shape in this technical solution refers to that the sample has a columnar overall contour with many irregular depressions and protrusions on its outer wall, and the outer circumferential wall of the annual floating plate can be fitted with the inner wall of the sleeve, but the inner circumferential wall of the floating plate cannot be fitted with the outer wall of the sample. Therefore, in the present technical solution, a rubber ring is arranged on the inner circumferential wall of the floating plate. The inner diameter of the rubber ring allows the normal passage of the heat-shrinkable film. The rubber ring has a certain deformation ability and can shorten the distance between the floating plate and the outer wall of the sample, which can ensure that most of the foam colloid in the annular space is unable to continue upward extension under the horizontal limit of the floating plate and the rubber ring, thereby minimizing the occurrence of non-foaming colloid filling on the outer wall of the sample and the heat-shrinkable film; at the same time, when encountering irregular protrusions on the outer wall of the sample, the rubber ring can directly cross over the protruded portion by means of its own flexibility.

A spray chamber is provided along the outer circumferential wall of the floating plate, the spray chamber is internally filled with a cleaning agent, a plurality of spray holes are provided on a lower surface of the spray chamber, and each spray hole is internally provided with an elastic opening-closing assembly. After the outer wall of the sample is wrapped with the formed foam colloid, the barrel and the base need to be removed from the sleeve and trimmed, on the premise of keeping both ends of the sample flat, the sleeve is placed on a clamping part of the seepage tester. The clamping part of the seepage tester includes two clamping discs, a sealing member and a water injection pipe, the two clamping discs are docked with the two ends of the sleeve, and the sealing member is used to seal the gap between the clamping discs and the sleeve, the water injection pipe starts to test the water seepage of the sample; after the test is completed, the foaming colloid in the sleeve needs to be cleaned in time. At this time, the barrel is placed inside the sleeve from the upper end of the sleeve, the cleaning agent is injected into the spray chamber, and as the injection pressure increases, the cleaning agent in the multiple discharge ports is sprayed onto the foaming colloid in the annular space. After the foaming colloid is separated from the inner wall of the sleeve, the floating plate, the discharge pipe and the upper surface of the base are cleaned, so as to continue the anti-seepage treatment of the side wall of the next sample.

The elastic opening-closing assembly includes a linkage rod matching the discharge port, an outer peripheral plate is arranged on the outer circumferential wall of one end of the linkage rod, a blind hole is provided in the middle part of the outer peripheral plate along the axis of the linkage rod, a plurality of discharge holes communicated with the blind hole are provided at the middle part of the linkage rod, a spring is provided between the outer peripheral plate and an inner wall of the spray chamber, a truncated cone-shaped flange is arranged on the outer circumferential wall of the other end of the linkage rod, and in the initial state, the outer wall of the linkage rod is attached to the inner wall of the discharge port, a large-diameter end face of the flange is attached to a lower surface of the spray chamber, and the plurality of discharge holes are placed in the spray hole. After the pressurized cleaning agent is injected into the spray chamber, the pressure in the spray chamber increases, and the cleaning agent will drive the linkage rod to move toward the outside of the spray hole after entering the blind hole. The cleaning agent is sprayed into the sleeve along the discharge holes communicated with the blind hole, wherein there are multiple discharge holes, that is, the sprayed cleaning agent will form multiple cone-shaped water curtains above the foaming colloid, which can ensure that the cleaning agent gradually moves down along the inner wall of the sleeve, to improve the cleaning efficiency of the foaming colloid, and after the foaming colloid is detached from the inner wall of the sleeve, the injection of the cleaning agent is stopped in time, the pressure inside the spray chamber is reduced, and the compressed spring will produce elastic recovery, and then drive the linkage rod to reset again, and at the same time, the discharge hole is also restored into the spray hole. The flange provided on the outer end of the linkage rod can prevent the linkage rod from being reset excessively, while in the initial state, the large-diameter end face of the flange is attached to the lower surface of the spray chamber, which can effectively prevent the leakage of cleaning agent and avoid the leakage of the cleaning agent from interfering with the foaming colloid when the next sample is subjected to anti-seepage treatment.

A follow-up ring made of rubber is provided circumferentially on the outer circumferential wall of the spray chamber. Optionally, the outer wall of the spray chamber and the inner wall of the sleeve conduct relative movement, and when the foaming material is foamed, it is necessary to realize the sealing between the outer wall of the spray chamber and the inner wall of the sleeve to prevent the foaming colloid from overflowing into the space between the outer wall of the spray chamber and the inner wall of the sleeve, the follow-up ring made of rubber can ensure the normal movement of the spray chamber in the vertical direction while sealing the gap between the outer wall of the spray chamber and the inner wall of the sleeve; at the same time, a sealing structure is also provided between the base and the sleeve to prevent the unfoamed liquid components from escaping through the bottom of the sleeve to prevent environmental pollution and achieve harmless treatment.

A plurality of annular rubber corrugated strips are provided radially on the outer peripheral wall of the barrel. Optionally, relative movement occurs between the outer wall of the barrel and the inner wall of the sleeve, and the sealing between the outer wall of the barrel and the inner wall of the sleeve needs to be realized when the foaming material is foamed, so as to prevent the foaming colloid from overflowing into the space between the outer wall of the barrel and the inner wall of the sleeve. The rubber follow-up ring can ensure the normal movement of the barrel in the vertical direction and at the same time seal the gap between the outer wall of the barrel and the inner wall of the sleeve.

Compared with the prior art, the present application has the following advantages and beneficial effects:

1. in the present application, the liquid in the discharge pipe is foamed before the mixed liquid at the bottom of the sleeve, and the formed foaming colloid is spirally wound on the outer wall of the heat-shrinkable film, and the foaming colloid formed after foaming of the liquid between the sample and the inner wall of the sleeve will completely fill the annular space, thereby ensuring that the outer wall of the sample is not only covered by the heat-shrinkable film, but at the same time, the foaming colloid always keeps squeezing the sample and the heat-shrinkable film, and the floating plate is always above the annular space between the sample and the inner wall of the sleeve to prevent the foaming colloid from changing randomly in the vertical upward direction and ensure that both ends of the sample are aligned after the anti-seepage treatment is completed, facilitating perfect docking with the detection part of the seepage tester;

2. in the present application, the liquid discharge speed of the liquid in the first phase liquid pipe and the second phase liquid pipe is controlled, and the liquid discharge height of the liquid in the first phase liquid pipe and the second phase liquid pipe is arranged to be different from the discharge height of the mixed liquid in the discharge pipe, thus ensuring that there is a minor difference between the forming speed of the foaming colloid in the annular space and that of the foaming colloid overflowing from the discharge port, so as to realize the goal of preliminary bondage of the heat-shrinkable film and the sample, and then the overall wrapping;

3. in the present application, there are multiple discharge holes, that is, the sprayed cleaning agent will form multiple cone-shaped water curtains above the foaming colloid, which can ensure that the cleaning agent gradually moves down along the inner wall of the sleeve, so as to improve the cleaning efficiency of the foaming colloid, and after the foaming colloid is detached from the inner wall of the sleeve, the injection of the cleaning agent is stopped in time, the pressure inside the spray chamber is reduced, and the compressed spring will produce elastic recovery, and then drive the linkage rod to reset again, and at the same time, the discharge hole is also restored into the discharge port. The flange provided on the outer end of the linkage rod can prevent the linkage rod from being reset excessively, while in the initial state, the large-diameter end face of the flange is attached to the lower surface of the spray chamber, which can effectively prevent the leakage of cleaning agent and avoid the leakage of the cleaning agent from interfering with the foaming colloid when the next sample is subjected to anti-seepage treatment.

BRIEF DESCRIPTION OF THE DRAWINGS

The drawings described here are used to provide a further understanding of the embodiments of the present application, and constitute a part of the present application, rather than limiting the embodiments thereof. In the attached drawings.

Reference signs: 1—rotation shaft, 2—barrel, 3—rubber corrugated strip, 4—primary lantern ring, 5—secondary lantern ring, 6—connecting rod, 7—first phase liquid pipe, 8—second phase liquid pipe, 9—electromagnetic valve, 10—mixing pipe, 11—sealing ring, 12—base, 13—annular groove, 14—sample, 15—sleeve, 16—follower-up ring, 17—floating plate, 18—magnetic ring, 19—heat-shrinkable film, 20—spray chamber, 21—spray hole, 22—discharge pipe, 23—discharge port, 24—liquid discharge hole, 25—rubber ring, 26—tertiary lantern ring, 27—baffle plate, 28—flange, 29—linkage rod, 30—blind hole, 31—spring, 32—outer peripheral plate.

DETAILED DESCRIPTION OF THE EMBODIMENTS

In order to make the purpose, technical solutions and advantages of the present application clearer, the present application will be further described in detail below in conjunction with the examples and accompanying drawings. The illustrative embodiments of the present application and their descriptions are only used to explain the present application, but not to limit the present application. It should be noted that the present application is already in the stage of actual development and use.

Embodiment 1

As shown in FIGS. 1 to 5, the device of this embodiment includes a sleeve 15 with both ends open, a barrel 2 arranged on an upper end of the sleeve 15, a base 12 arranged below the barrel 2, a primary lantern ring 4, a secondary lantern ring 5, wherein a tertiary lantern ring 26 and a rotation shaft 1 are fixedly arranged in the barrel 2 along the radial direction of the barrel 2 in sequence from the outside inward, a lower end surface of the barrel 2 is provided with an annular floating plate 17, each of the primary lantern ring 4, the secondary lantern ring 5, and the tertiary lantern ring 26 are internally hollow, at least one first phase liquid pipe 7 is arranged on a lower end surface of the primary lantern ring 4, and at least one second phase liquid pipe 8 is arranged on a lower end surface of the secondary lantern ring 5, lower ends of the first phase liquid pipe 7 and the second phase liquid pipe 8 extend vertically downward after passing through the floating plate 17.

Figure 1:
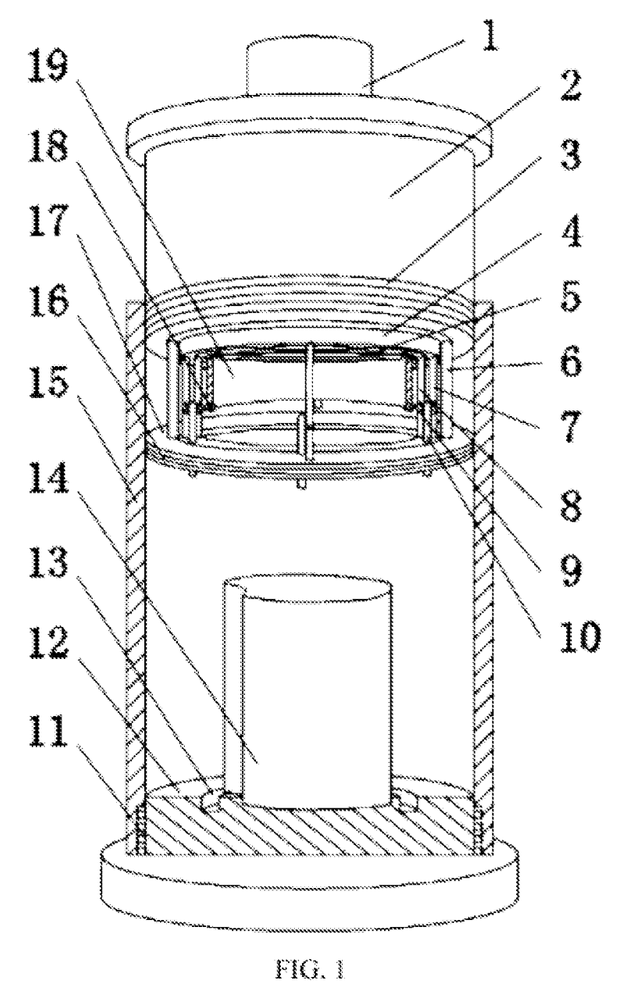
FIG. 1 is a structural diagram of the present application.
Figure 2:
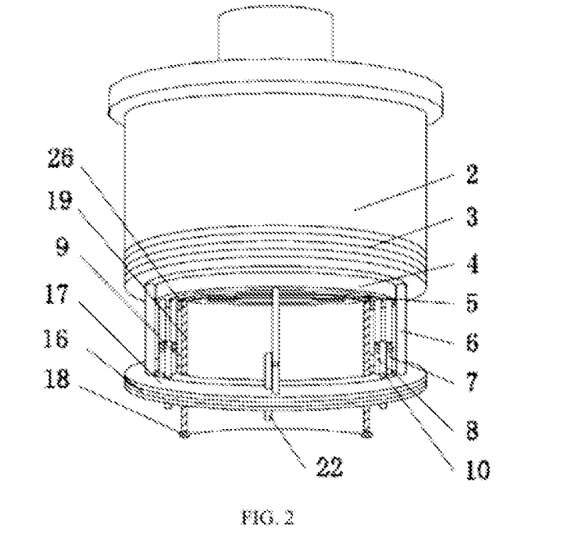
FIG. 2 is a structural diagram of a lifting barrel.
Figure 4:
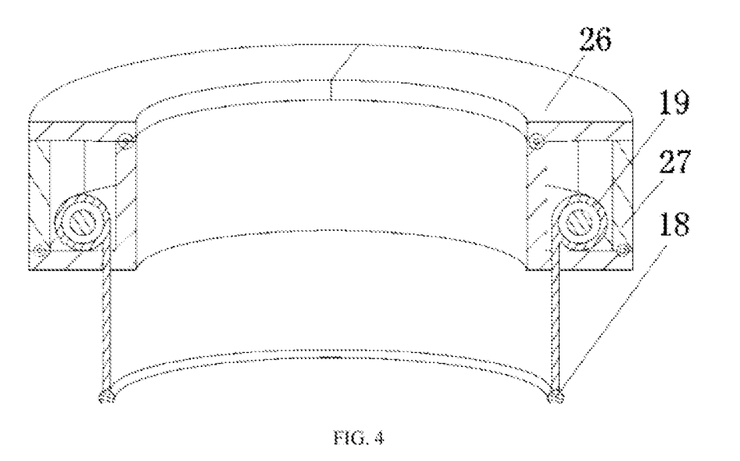
FIG. 4 is a structural diagram of a tertiary lantern ring.

A winding ring is circumferentially arranged in the tertiary lantern ring 26, a heat-shrinkable film 19 has one end circumferentially wound on an outer circumferential wall of the winding ring, and the other end extending downward after movably running through a lower end surface of the tertiary lantern ring 26 and a middle part of the floating plate 17, the floating plate 17 is provided with a mixing pipe 10 which is communicated with the first phase liquid pipe 7 and the second phase liquid pipe 8 respectively, a lower end of the mixing pipe 10 runs through the floating plate 17 and is provided with a discharging pipe 22, the discharging pipe 22 has a closed lower end and is provided with a discharge port 23 facing a center line of the barrel 2 on a side wall.

In the embodiment, during the specific operation, the base 12 completely seals the lower end of the sleeve 15, an irregular sample 14 is placed on the upper surface of the base 12, the barrel 2 is vertically inserted into the sleeve 15, and an external motor drives the rotation shaft 1 and the barrel 2 to move in a circumferential direction, while an external cylinder drives the barrel 2 to move up and down in the sleeve 15, and a floating plate 17 is provided below the barrel 2 through a connecting rod 6, and the distance between the lower end surface of the barrel 2 and the upper surface of the floating plate 17 can be changed by changing the length of the connecting rod 6. When performing anti-seepage treatment, a heat-shrinkable film 19 is first removed from the tertiary lantern ring 26 and moves vertically downward along the axis of the barrel 2, and the columnar heat-shrinkable film 19 is directly sleeved on the periphery of the sample 14 after passing through the middle of the floating plate 17, until the lower end of the heat-shrinkable film 19 wraps the irregular sample 14 completely, the heat-shrinkable film 19 stops moving, and at the same time the barrel 2 and the floating plate 17 move down to near the upper surface of the base 12, at this point, the interior of the primary lantern ring 4 is filled with a component liquid A, the secondary lantern ring 5 is filled with a component liquid B, a liquid discharge hole 24 communicated with the first phase liquid pipe 7 and the second phase liquid pipe 8 is arranged on the bottom of the floating plate 17, the two component liquid enter the sleeve 15 through the first phase liquid pipe 7 and the second phase liquid pipe 8 respectively. The floating plate 17 is also provided with a mixing pipe 10 which is communicated with the first phase liquid pipe 7 and the second phase liquid pipe 8 respectively. A discharge pipe 22 is located below the floating plate 17, and a discharge port 23 of the discharge pipe 22 is facing the axis of the floating plate 17. The external motor drives the barrel 2 to rotate slowly while the external cylinder drives the barrel 2 to move upward, and a pressurized pipe is connected to the mixing pipe 10 to ensure that the flow rate and flow velocity of the two component liquid flowing from the mixing pipe 10 into the discharge pipe 22 are greater than the liquid flow rate in the first phase liquid pipe 7 and the second phase liquid pipe 8, that is, the foam material ejected from the discharge port 23 is formed in a short time, and the liquids in the first phase liquid pipe 7 and the second phase liquid pipe 8 start to produce a chemical reaction at the bottom of the barrel 2, and the heat released therefrom can heat the heat-shrinkable film 19 covering the sample 14 step by step from top to bottom along the axis of the barrel 2, so that the columnar heat-shrinkable film 19 is tightly attached to the outer wall of the sample 14, and at the same time, the liquid in the discharge pipe 22 is foamed before the mixed liquid at the bottom of the sleeve 15, and the formed foaming colloid is wound on the outer wall of the heat-shrinkable film 19 in a spiral state, and the foaming colloid formed by the liquid between the sample 14 and the inner wall of the sleeve 15 will completely fill the annular space, so as to ensure that the outer wall of the sample 14 is covered by the heat-shrinkable film 19, while the foaming colloid keeps squeezing the sample 14 and the heat-shrinkable film 19, and the floating plate 17 is kept above the annular part between the sample 14 and the inner wall of the sleeve 15, to prevent the foaming colloid from changing irregularly in the vertical upward direction, ensure that the two ends of the sample 14 after the anti-seepage treatment are flush, and facilitate the perfect docking with the detection part of the seepage tester.

Figure 3:
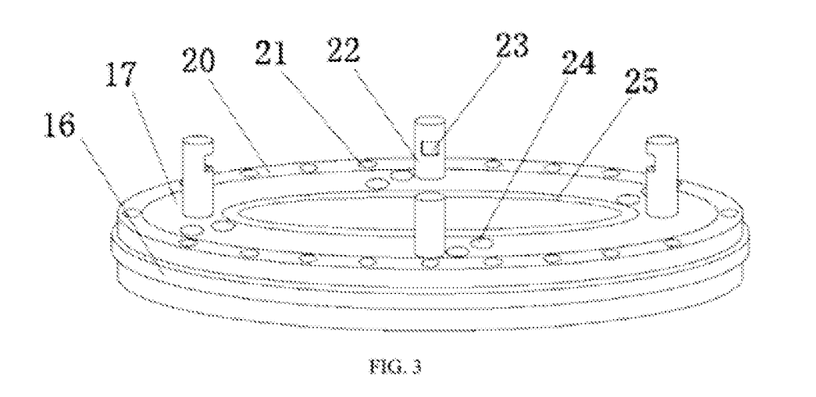
FIG. 3 is a bottom view of a floating plate.

It should be pointed out that the overflow speed of the formed foaming colloid from the discharge port 23 is relatively fast, and the formed foaming colloid moves circumferentially together with the barrel 2. Therefore, spiral ribs are formed on the outer wall of the heat-shrinkable film 19. In this technical solution, there can be multiple first phase liquid pipes 7 and multiple second phase liquid pipes 8, the number of the mixing pipe 10 is the same as that of the first phase liquid pipe 7, and one individual first phase liquid pipe 7, one mixing pipe 10 and one second phase liquid pipe 8 form one group, so that there are multiple discharge pipes 22 likewise which are evenly distributed on the lower end surface of the floating plate 17, the lower ends of the multiple discharge pipes 22 are at horizontal heights which increase or decrease progressively. For example, if any one of the discharge pipes 22 is used as a base point, the lower end of the discharge pipe 22 on the base point is located at a highest horizontal height, and the lower ends of the remaining discharge pipes 22 are located at horizontal heights which decrease successively, in the present technical solution, the horizontal height refers to the distance between the lower end surface of the discharge pipe 22 and the upper surface of the base 12 in the initial state; when there are multiple discharge pipes 22, a plurality of spiral ribs are formed on the outer wall of the heat-shrinkable film 19, by means of the expansion of the ribs themselves and the expansion and extrusion of the foaming colloid in the annular space, the plurality of ribs closely adhere to the heat-shrinkable film 19 until the floating plate 17 moves upward to a point where the floating plate 17 is flush with the upper end surface of the sample 14. At this time, the annular space between the sample 14 and the sleeve 15 is filled with the foaming colloid, and the region beyond the upper and lower end surfaces of the sample 14 is defined by the floating plate 17 and the base 12 and therefore kept free of the foaming colloid, so as to facilitate docking with the clamping part of the seepage tester. For the multiple ribs formed on the outer wall of the heat-shrinkable film 19, it is formed a little faster than the foaming colloid formed by mixing of the liquid in the first phase liquid pipe 7 and the second phase liquid pipe 8, therefore there is no gap after the two foaming colloids are mixed, ensuring that the foaming colloid finally formed in the annular space can seamlessly wrap the side wall of the sample 14. And the heat-shrinkable film 19 can be preliminarily restrained and tightly wrapped in the vertical direction by multiple spiral foaming colloids, so as to prevent the irregular expansion of the foaming colloid in the annular space from tearing the heat-shrinkable film 19 when the foaming colloid is not in contact with the bottom of the floating plate 17, thus ensuring the integrity of the heat-shrinkable film 19.

In addition, an electromagnetic valve 9 is provided in the first phase liquid pipe 7 and the second phase liquid pipe 8, respectively, by keeping the liquid in the annular space and the mixed liquid in the discharge pipe 22 at different release speeds, the forming speed of the foaming colloid in the discharge pipe 22 and the foaming colloid in the annular space can be controlled intuitively and effectively, thereby fulfilling the purpose of anti-seepage treatment on the side wall of the sample 14.

Optionally, the outer wall of the spray chamber 20 moves relative to the inner wall of the sleeve 15, and the sealing between the outer wall of the spray chamber 20 and the inner wall of the sleeve 15 needs to be realized during foaming of the foaming material, so as to prevent the foaming colloid from overflowing to the space between the outer wall of the spray chamber 20 and the inner wall of the sleeve 15, and the follow-up ring 16 made of rubber can ensure that the spray chamber 20 moves normally in the vertical direction while sealing the gap between the outer wall of the spray chamber 20 and the inner wall of the sleeve 15; at the same time, a plurality of sealing rings 11 are correspondingly arranged between the base 12 and the sleeve 15 to prevent the unfoamed liquid components from escaping outward through the bottom of the sleeve 15, preventing environmental pollution, and achieving harmless treatment.

Optionally, relative movement occurs between the outer wall of the barrel 2 and the inner wall of the sleeve 15, and the sealing between the outer wall of the barrel 2 and the inner wall of the sleeve 15 needs to be realized when the foaming material is foamed, so as to prevent the foaming colloid from overflowing into the space between the outer wall of the barrel 2 and the inner wall of the sleeve 15. The follow-up ring 16 made of rubber can ensure the normal movement of the barrel 2 in the vertical direction and at the same time seal the gap between the outer wall of the barrel 2 and the inner wall of the sleeve 15.

Optionally, the liquid discharge speed of the liquid in the first phase liquid pipe 7 and the second phase liquid pipe 8 is controlled, and the liquid discharge height of the liquid in the first phase liquid pipe 7 and the second phase liquid pipe 8 is arranged to be different from the discharge height of the mixed liquid in the discharge pipe 22, thus ensuring that there is a minor difference between the forming speed of the foaming colloid in the annular space and that of the foaming colloid overflowing from the discharge port 23, so as to realize the goal of preliminary bondage of the heat-shrinkable film 19 and the sample 14, and then the overall wrapping.

Embodiment 2

As shown in FIGS. 1 to 5, on the basis of Embodiment 1, in this embodiment, a magnetic ring 18 is provided on an extension end of the heat-shrinkable film 19, an annular groove 13 matching the magnetic ring 18 is provided on an upper surface of the base 12. A rubber ring 25 is arranged circumferentially on the inner circumferential wall of the floating plate 17, and the inner diameter of the rubber ring 25 is larger than the outer diameter of the magnetic ring 18. The magnetic ring 18 arranged at the lower end of the heat-shrinkable film 19 can not only increase the weight at the lower end of the heat-shrinkable film 19, but also attract the metal annual groove 13 arranged on the upper surface of the base 12 to prevent the foaming colloid in the annular space from passing through the bottom of the sample 14, while ensuring that the heat-shrinkable film 19 in the tertiary lantern ring 26 protrudes freely during the upward movement of the barrel 2, and the lower end of the heat-shrinkable film 19 attached to the upper surface of the base 12 will not be displaced with the upward movement of the barrel 2. In order to facilitate the replacement of the heat-shrinkable film, in this embodiment, the upper end surface of the tertiary lantern ring is arranged as an open structure, and the open end is blocked by a cover plate, specifically, the cover plate is formed by splicing a plurality of arc-shaped plates to form a complete annual plate, and multiple arc-shaped plates are hinged with the side wall of the tertiary lantern ring, so as to facilitate real-time observation or replacement of heat-shrinkable film.

Because the sample 14 has an irregular shape, the irregular shape in this technical solution refers to that the sample 14 has a columnar overall contour with many irregular depressions and protrusions on its outer wall, and the outer circumferential wall of the annual floating plate 17 can be fitted with the inner wall of the sleeve 15, but the inner circumferential wall of the floating plate 17 cannot be fitted with the outer wall of the sample 14. Therefore, in the present technical solution, a rubber ring 25 is arranged on the inner circumferential wall of the floating plate 17. The inner diameter of the rubber ring 25 allows the normal passage of the heat-shrinkable film 19. The rubber ring 25 has a certain deformation ability and can shorten the distance between the floating plate 17 and the outer wall of the sample 17, which can ensure that most of the foam colloid in the annular space is unable to continue upward extension under the horizontal limit of the floating plate 17 and the rubber ring 25, thereby minimizing the occurrence of non-foaming colloid filling on the outer walls of the sample 14 and the heat-shrinkable film 19; at the same time, when encountering irregular protrusions on the outer wall of the sample 14, the rubber ring 25 can directly cross over the protruded portion by virtue of its own flexibility.

Embodiment 3

As shown in FIGS. 1 to 5, on the basis of Embodiment 1, in the present embodiment, a spray chamber 20 is provided along the outer circumferential wall of the floating plate 17, the spray chamber 20 is internally filled with a cleaning agent, a plurality of spray holes 21 are provided on a lower surface of the spray chamber 20, and each spray hole 21 is internally provided with an elastic opening-closing assembly. The elastic opening-closing assembly includes a linkage rod 29 matching the discharge port 23, an outer peripheral plate 32 is arranged on the outer circumferential wall of one end of the linkage rod 29, a blind hole 30 is provided in the middle part of the outer peripheral plate 32 along the axis of the linkage rod 29, a plurality of discharge holes communicated with the blind hole 30 are provided at the middle part of the linkage rod 29, a spring 31 is provided between the outer peripheral plate 32 and an inner wall of the spray chamber 20, a truncated cone-shaped flange 28 is arranged on the outer circumferential wall of the other end of the linkage rod 29, and in the initial state, the outer wall of the linkage rod 29 is attached to the inner wall of the spray hole 21, a large-diameter end face of the flange 28 is attached to a lower surface of the spray chamber 20, and the plurality of discharge holes 24 are placed in the spray chamber 20.

After the outer wall of the sample 14 is wrapped with the formed foam colloid, the barrel 2 and the base 12 are removed from the sleeve 15 and trimmed, on the premise of keeping both ends of the sample 14 flat, the sleeve 15 is placed on a clamping part of a seepage tester. The clamping part of the seepage tester includes two clamping discs, a sealing member and a water injection pipe, the two clamping discs are docked with the two ends of the sleeve 15, and the sealing member is used to seal the gap between the clamping discs and the sleeve 15, the water injection pipe starts to test the water seepage of the sample 14; after the test is completed, the foaming colloid in the sleeve 15 needs to be cleaned in time. At this time, the barrel 2 is placed inside the sleeve 15 from the upper end of the sleeve 15, the cleaning agent is injected into the spray chamber 20, and as the injection pressure increases, the cleaning agent in the multiple discharge holes 21 is sprayed onto the foaming colloid in the annular space. After the foaming colloid is separated from the inner wall of the sleeve 15, cleaning is performed to the floating plate 17, the discharge pipe 22 and the upper surface of the base 12, so as to continue the anti-seepage treatment of the side wall of the next sample 14.

Figure 5:
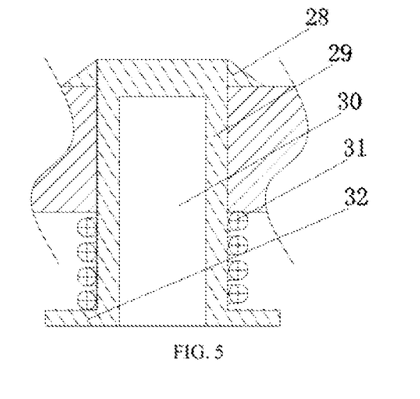
FIG. 5 is a structural diagram of an elastic opening-closing assembly.

After the pressurized cleaning agent is injected into the spray chamber 20, the pressure in the spray chamber 20 increases, and the cleaning agent will drive the linkage rod 29 to move toward the outside of the spray hole 21 after entering the blind hole 30. The cleaning agent is sprayed into the sleeve 15 along the spray holes 21 communicated with the blind hole 30, wherein there are multiple spray holes 21, that is, the sprayed cleaning agent will form multiple cone-shaped water curtains above the foaming colloid, which can ensure that the cleaning agent gradually moves down along the inner wall of the sleeve 15, to improve the cleaning efficiency of the foaming colloid assisting artificial machinery, and after the foaming colloid is detached from the inner wall of the sleeve 15, the injection of the cleaning agent is stopped in time, the pressure inside the spray chamber 20 is reduced, and the compressed spring 31 will produce elastic recovery, and then drive the linkage rod 29 to reset again, and at the same time, the discharge hole is also restored into the spray holes 21. The flange 28 provided on the outer end of the linkage rod 29 can prevent the linkage rod 29 from being reset excessively, while in the initial state, the large-diameter end face of the flange 28 is attached to the lower surface of the spray chamber 20, which can effectively prevent the leakage of cleaning agent and avoid the leakage of the cleaning agent from interfering with the foaming colloid when the next sample 14 is subjected to anti-seepage treatment.

The specific embodiments described above have further described the purpose, technical solutions and beneficial effects of the present application in detail. It should be understood that the above descriptions are only specific embodiments of the present application and are not intended to limit the scope of the present application. Any modification, equivalent replacement, improvement, etc., made within the spirit and principles of the present application shall be included in the protection scope of the present application.

What is claimed is:

1. A reversible plugging-type device for preventing seepage from a side wall of an irregular sample, comprising a sleeve (15) with both ends open, a barrel (2) arranged on an upper end of the sleeve (15), a base (12) arranged below the sleeve (15), wherein, a primary lantern ring (4), a secondary lantern ring (5), a tertiary lantern ring (26) and a rotation shaft (1) are fixedly arranged in the barrel (2) along the radial direction of the barrel (2) in sequence from the outside inward, a lower end surface of the barrel (2) is provided with an annular floating plate (17), each of the primary lantern ring (4), the secondary lantern ring (5), and the tertiary lantern ring (26) are internally hollow, at least one first phase liquid pipe (7) is arranged on a lower end surface of the primary lantern ring (4), and at least one second phase liquid pipe (8) is arranged on a lower end surface of the secondary lantern ring (5), lower ends of the first phase liquid pipe (7) and the second phase liquid pipe (8) extend vertically downward toward a mixing pipes (10); the primary lantern ring (4) is internally filled with a component liquid A, the secondary lantern ring (5) is internally filled with a component liquid B, and the two component liquid enter into the sleeve (15) through the first phase liquid pipe (7) and the second phase liquid pipe (8), respectively, the component liquid A is a mixed liquid of a foaming agent, a foam stabilizer, a catalyst and polyether polyol, and the component liquid B is isocyanate;

a winding ring is arranged circumferentially in the tertiary lantern ring (26), a heat-shrinkable film (19) has one end circumferentially wound on an outer circumferential wall of the winding ring, and the other end extending downward after running through a lower end surface of the tertiary lantern ring (26) and a middle part of the floating plate (17), the floating plate (17) is provided with a mixing pipe (10) which is communicated with the first phase liquid pipe (7) and the second phase liquid pipe (8) respectively, a lower end of the mixing pipe (10) runs through the floating plate (17) and is provided with a discharging pipe (22), the discharging pipe (22) has a closed lower end and is provided with a discharge port (23) facing a center line of the barrel (2) on a side wall.

2. The reversible plugging-type device for preventing seepage from a side wall of an irregular sample of claim 1, wherein, an electromagnetic valve (9) is arranged in the first phase liquid pipe (7) and the second phase liquid pipe (8) respectively, and located below a portion where the mixing pipe (10) is respectively connected with the first phase liquid pipe (7) and the second phase liquid pipe (8).

3. The reversible plugging-type device for preventing seepage from a side wall of an irregular sample of claim 1, wherein, the horizontal heights of the lower end of the first phase liquid pipe (7) and the lower end of the second phase liquid pipe (8) are higher than the horizontal height of the discharge port (23).

4. The reversible plugging-type device for preventing seepage from a side wall of an irregular sample of claim 1, wherein, a magnetic ring (18) is provided on an extension end of the heat-shrinkable film (19), an annular groove (13) matching the magnetic ring (18) is provided on an upper surface of the base (12).

5. The reversible plugging-type device for preventing seepage from a side wall of an irregular sample of claim 4, wherein, a rubber ring (25) is circumferentially provided on the inner circumferential wall of the floating plate (17) and has an inner diameter greater than the outer diameter of the magnetic ring (18).

6. The reversible plugging-type device for preventing seepage from a side wall of an irregular sample of claim 1, wherein, a spray chamber (20) is provided along the outer circumferential wall of the floating plate (17), and internally filled with a cleaning agent, a plurality of spray holes (21) are provided on a lower surface of the spray chamber (20), and each spray hole (21) is internally provided with an elastic opening-closing assembly.

7. The reversible plugging-type device for preventing seepage from a side wall of an irregular sample of claim 6, wherein, the elastic opening-closing assembly includes a linkage rod (29) matching the spray holes (21), an outer peripheral plate (32) is arranged on the outer circumferential wall of one end of the linkage rod (29), a blind hole (30) is provided in the middle part of the outer peripheral plate (32) along the axis of the linkage rod (29), a plurality of discharge holes communicated with the blind hole (30) are provided at the middle part of the linkage rod (29), a spring (31) is provided between the outer peripheral plate (32) and an inner wall of the spray chamber (20), a truncated cone-shaped flange (28) is arranged on the outer circumferential wall of the other end of the linkage rod (29), and in the initial state, the outer wall of the linkage rod (29) is attached to the inner wall of the spray hole (21), a large-diameter end face of the flange (28) is attached to a lower surface of the spray chamber (20), and the plurality of discharge holes are placed in the spray hole (21).

8. The reversible plugging-type device for preventing seepage from a side wall of an irregular sample of claim 6, wherein, a follow-up ring (16) made of rubber is provided circumferentially on the outer circumferential wall of the spray chamber (20).

9. The reversible plugging-type device for preventing seepage from a side wall of an irregular sample of claim 1, wherein, a plurality of annular rubber corrugated strips (3) are provided radially on the outer peripheral wall of the barrel (2).

\* \* \* \* \*